US00PP11100P

United States Patent [19]

Fruehwirth

[11] Patent Number: Plant 11,100

[45] Date of Patent: Oct. 19, 1999

[54] POINSETTIA PLANT NAMED 'SNOWCAP'

[75] Inventor: Franz Fruehwirth, Encinitas, Calif.

[73] Assignee: Paul Ecke Ranch, Inc., Encinitas, Calif.

[21] Appl. No.: 09/004,042

[22] Filed: Jan. 7, 1998

[51] Int. Cl.[6] ..... A01H 5/00

[52] U.S. Cl. ..... Plt./304

[58] Field of Search ..... Plt./304, 303, 305

[56] References Cited

U.S. PATENT DOCUMENTS

P.P. 8,125 2/1993 Fruehwirth ..... Plt./304
P.P. 8,126 2/1993 Fruehwirth ..... Plt./304
P.P. 8,319 7/1993 Dahlquist ..... Plt./304

*Primary Examiner*—Howard J. Locker
*Assistant Examiner*—Kent L. Bell
*Attorney, Agent, or Firm*—Arnold, White & Durkee

[57] ABSTRACT

Poinsettia 'Snowcap' is a new cultivar, distinguished by creamy white flower bracts, medium dark green foliage, self-branching characteristics, and 9-week flowering response time. The flower bract color is whiter than most poinsettias in commerce. The new plant produces a very desirable branched flowering pot plant for the holiday season market. 'Snowcap' is resistant to epinasty after being confined to shipping containers. The post-production foliage and bract retention is excellent even under low light intensities in the consumer's home.

1 Drawing Sheet

BACKGROUND OF THE PLANT

This new poinsettia cultivar, 'Snowcap', originated as an induced self-branching sport of a seedling known as "L-16" (not patened) in my greenhouse in Encinitas, Calif. "L-16" is a proprietary plant and there are no specimens in the public domain. 'Snowcap' was selected because of its creamy, white flower bracts, large flower clusters, medium dark green foliage, mid- season flowering response and self branching characteristics; traits which distinguish it from other poinsettia cultivars, and seem to make it a desirable plant for commercial greenhouse production. It has whiter flower bracts than most "white" poinsettias in commerce. After selection, 'Snowcap' was vegetatively reproduced from stem cuttings for test purposes in Encinitas, Calif. By subjecting clones of this plant to successive generations of vegetative propagation, it was demonstrated that the distinctive characteristics of 'Snowcap' held true from generation to generation.

BRIEF DESCRIPTION OF THE PHOTOGRAPHS

Poinsettia 'Snowcap' is illustrated in the accompanying color photographs.

The upper photograph is a side view of one branched plant per pot in full flower.

The lower photograph is a top view of the same plant showing flower and bract formation.

DESCRIPTION OF THE PLANT

The following is a detailed description of this new poinsettia as observed in Encinitas, CA, U.S.A. during December 1996. Observations were recorded from flowering plants, grown as one branched plant per pot. The pot was 14 cm in diameter and 11 cm in height. Color designations are compared to the 1986 edition of R.H.S. Colour Chart, first published in 1966 by The Royal Horticultural Society, London, England.

THE PLANT

Origin: Sport of a seedling. The sport was induced by application of the procedures set forth in U.S. Pat. No. 4,724,276 to the seedling plant. Rootstock used was 'Angelika' (U.S. Plant Pat. No. 5,492).

Classification:

*Botanic.*—*Euphorbia pulcherrima* Willd.

*Common name.*—Poinsettia.

*Cultivar name.*—'Snowcap'.

Form: Shurb.

Height: Short to medium.

Growth habit: As a single stemmed plant, upright and vigorous with self-branching side shoots. The application of a chemical growth retardant may not be needed to restrict height for commercial pot plant production. I observed one branched plant in a pot with an overall height of 41 cm and an overall width of 57 cm. The diameter of individual inflorescenses is 26 cm.

Branching: Axillary branches will develop and terminate in an inflorescence without pinching. However, it is usually desirable to pinch 'Snowcap' before inflorescence induction and remove all terminal dominance. Then, all axillary branches will develop uniformly and at a faster rate.

Growth rate: Rooting of stem cutting occurs in 12–18 days under intermittent mist. The plant will flower in about nine weeks under continuous long night conditions and night temperatures of about 16–18°C.

Foliage: The foliage is clean and uniformly medium dark green from bottom to top of the plant. The leaves are of medium size, leaf blades typically being 14 cm long and 9 cm wide with leaf petioles 5–6 cm long.

*Leaf shape.*—Typicaly leaves are generally ovate with obtuse bases and acuminate tips. Leaf margins are sometimes lobed with 1 indentation on each side of the leaf blade.

*Color.*—Upper side—Dark medium green, darker than R.H.S. 137A and near 147A. Under side—Green, near R.H.S. 147A.

*Retention.*—The foliage lasts extremely well even under low light intensities in the comsumer's home.

Bracts: Generally there are 20–22 white bracts of various sizes subtending the cyathia. The primary bracts have blades typically 12–13 cm long and 7–8 cm wide with petioles about 4 cm long.

*Shape.*—Primary bracts are ovate with acute bases and acuminate tips. Bract margins are entire. Secondary bracts of various sizes are broadly elliptic.

*Color.*—Upper side—White, whiter than R.H.S. 2D. Under side—White, near R.H.S. 2D, with greenish veins.

Flowers: Generally, 21–24 cyathia (flowers) per inflorescence are present when the plant is in full bloom. Each cyathium is about 6 mm long and 5 mm wide, green in color, and fringed creamy white at the distal end. One or two yellow nectar cups protrude from the side of each cyathium. The flower pedicel is also green and about 5 mm in length. The stamens protruding from the cyathia are white. The anthers are bifurcate; the pollen is yellow and copious. The stigmas are creamy white and trifurcate.

*Cyathium.*—Cyathium retention is better than average, lasting three weeks beyond fully mature flowers.

*Nectar exudate.*—Abundant.

*Seeds.*—Self-incompatible.

*Fertility.*—Not observed.

*Disease resistance.*—Typical of the species.

Post production: Poinsettia 'Snowcap' is resistant to epinasty after being confined to shipping containers and retains its leaves and flower bracts for several weeks in the consumer's home environment.

What is claimed is:

1. A new and distinct Poinsettia plant, substantially as herein shown and described, distinguished by its creamy white flower bracts, medium dark green foliage and self-branching characteristics.

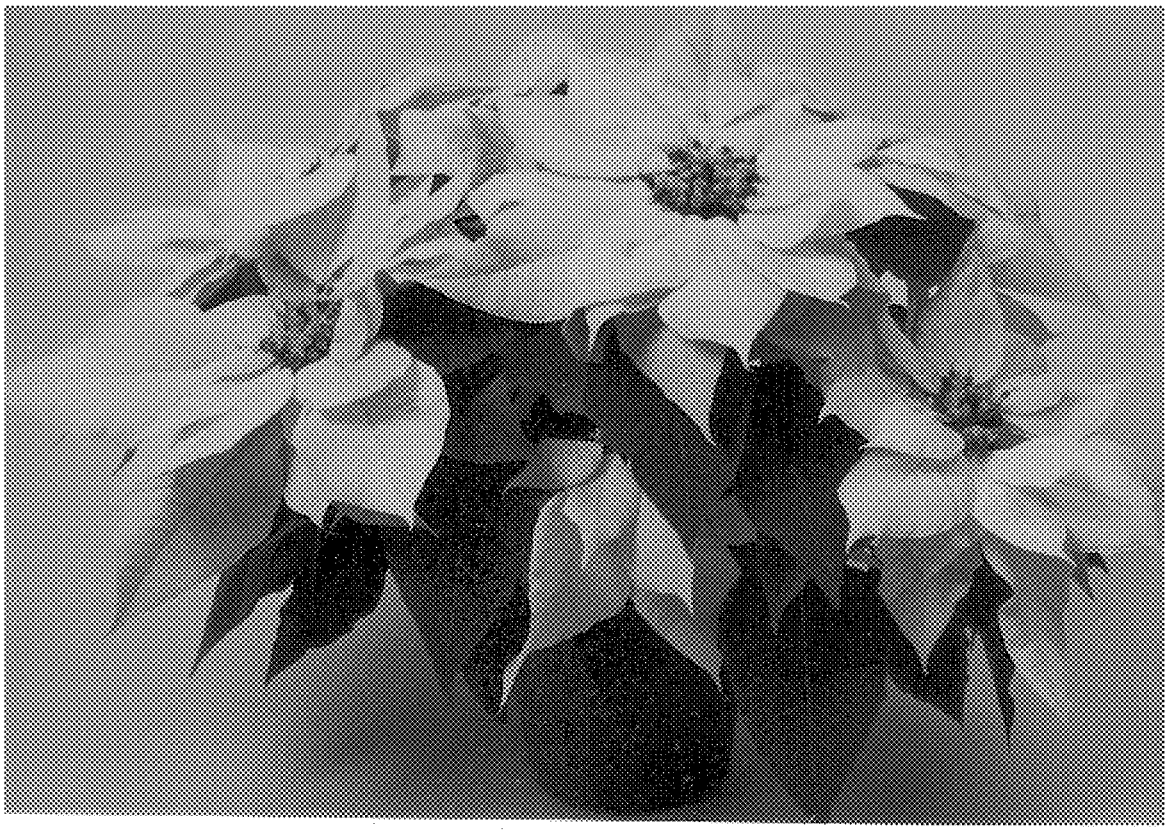
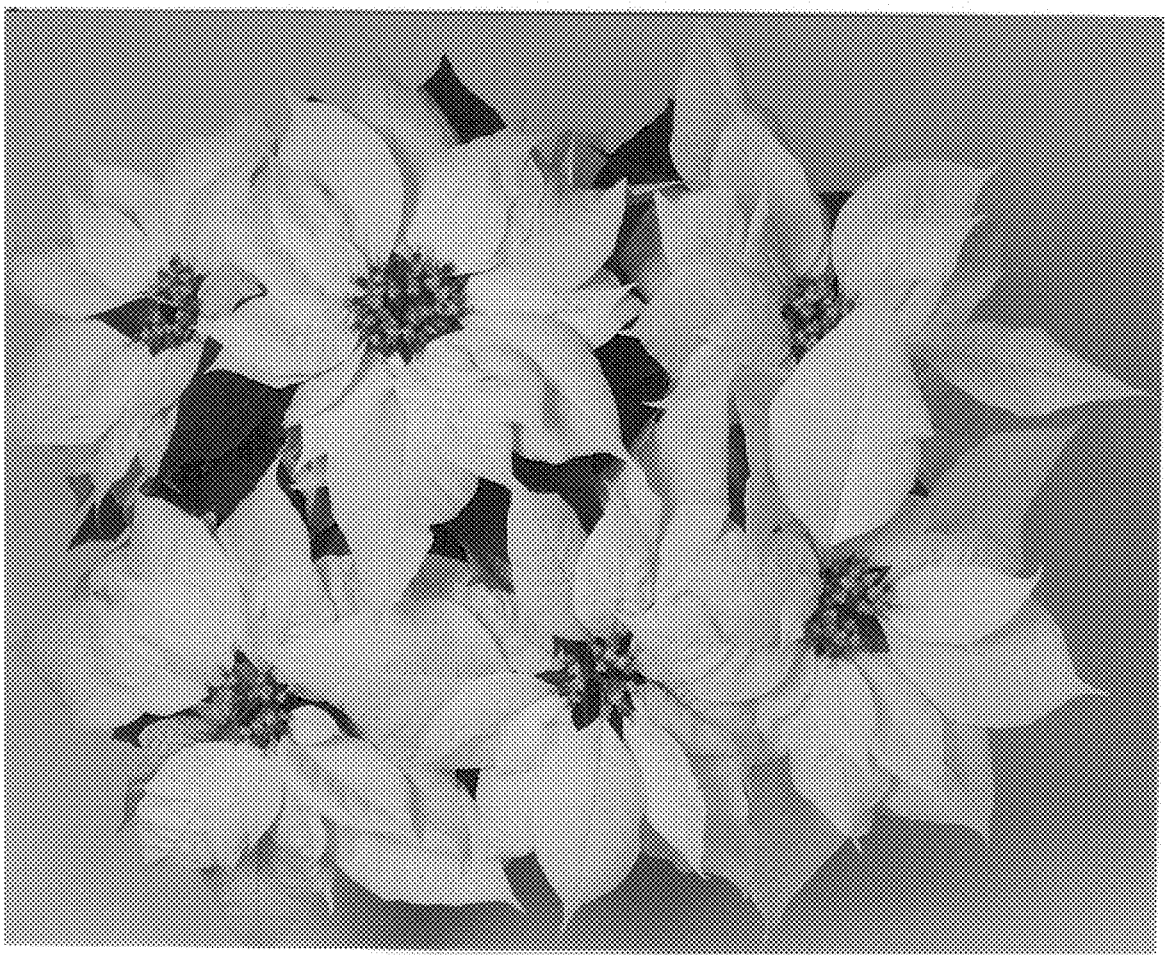

* * * * *